(12) United States Patent
Staels

(10) Patent No.: US 7,368,286 B2
(45) Date of Patent: May 6, 2008

(54) METHOD AND DEVICE FOR IDENTIFYING SUBSTANCES CAPABLE OF MODULATING ADIPOCYTE DIFFERENTIATION

(75) Inventor: Bart Staels, Petit Enghien (BE)

(73) Assignee: Genfit, Loos (FR)

(*) Notice: Subject to any disclaimer, the term of this patent is extended or adjusted under 35 U.S.C. 154(b) by 418 days.

(21) Appl. No.: 10/501,525

(22) PCT Filed: Jan. 17, 2003

(86) PCT No.: PCT/FR03/00157

§ 371 (c)(1),
(2), (4) Date: Jul. 16, 2004

(87) PCT Pub. No.: WO03/060106

PCT Pub. Date: Jul. 24, 2003

(65) Prior Publication Data

US 2005/0032064 A1 Feb. 10, 2005

(30) Foreign Application Priority Data

Jan. 18, 2002 (FR) .................................. 02 00582

(51) Int. Cl.
*C12N 5/10* (2006.01)
(52) U.S. Cl. ...................... 435/325; 435/377; 435/440; 435/455
(58) Field of Classification Search .................... None
See application file for complete search history.

(56) References Cited

FOREIGN PATENT DOCUMENTS

| WO | WO 99/67637 | 12/1999 |
|---|---|---|
| WO | WO 02/058532 | 8/2002 |

OTHER PUBLICATIONS

Austin et al, "Induction of the Nuclear Orphan Receptor RORγ during Adipocyte Differentiation of D1 and 3T3-L1 Cells", Cell Growth and Differentiation, vol. 9, Mar. 1998, pp. 267-276.

Adelmant et al, "A functional Rev-erbα responsive element located in the human Rev-erbα promoter mediates a repressing activity", Proceedings of the National Academy of Sciences, vol. 93, Apr. 1996, pp. 3553-3558.

Database Accession No. P20393, XP002226720, Feb. 1, 1991.

Chawla et al, "Induction of Rev-ErbAα, an Orphan Receptor Encoded on the Opposite Strand of a α-Thyroid Hormone Receptor Gene, during Adipocyte Differentiation", The Journal of Biological Chemistry, vol. 268, No. 22, 1993, pp. 16265-16269.

Chawla et al, "Peroxisome proliferator and retinoid signaling pathways co-regulate preadipocyte phenotype and survival", Proceedings of the National Academy of Sciences, vol. 91, No. 5, Mar. 1, 1994, pp. 1786-1790.

Gervois et al, "Fibrates Increase Human REV-ERBα Expression in Liver via a Novel Peroxisome Proliferator-Activated Receptor Response Element", Molecular Endocrinology, vol. 13, Mar. 1999, pp. 400-409.

Fontaine et al, "The Orphan Nuclear Recdeptor Rev-Erbα Is a Peroxisome Proliferator-activated Receptor (PPAR) γ Target Gene and Promotes PPAR γ-induced Adipocyte Differentiation", The Journal of Biological Chemistry, vol. 278, No. 39, Sep. 26, 2003, pp. 37672-37680.

*Primary Examiner*—Manjunath Rao
*Assistant Examiner*—Daniel C Gamett
(74) *Attorney, Agent, or Firm*—Nixon & Vanderhye P.C.

(57) ABSTRACT

The invention concerns a method for identifying compounds capable of modulating adipocyte differentiation, which consists in contacting a compound to be tested with genetically modified pre-adipocyte cells overexpressing the REV-ERB ALPHA receptor and measuring the adipocyte differentiation of said genetically modified cells as compared with the adipocyte differentiation of same said genetically modified pre-adipocyte cells in the absence of said compound to be tested.

The invention also concerns genetically modified pre-adipocyte cells overexpressing the REV-ERB ALPHA receptor as well as the method for preparing said cells.

26 Claims, 4 Drawing Sheets

METHOD AND DEVICE FOR IDENTIFYING SUBSTANCES CAPABLE OF MODULATING ADIPOCYTE DIFFERENTIATION

This application is the U.S. national phase of international application PCT/FR03/00157 filed 17 Jan. 2003 which designated the U.S. and claims benefit of FR 02/00582, dated 18 Jan. 2002, the entire content of which is hereby incorporated by reference.

Insert the attached Sequence Listing in place of the Sequence Listing of the published application.

The present invention concerns methods for screening active molecules, in particular molecules having an activity in modulating adipocyte differentiation. The invention also concerns genetic constructs, cells and compositions useful for carrying out such screening methods, for example genetically modified pre-adipocyte cells overexpressing the REV-ERB ALPHA receptor, and methods for preparing said cells. The invention is useful for identifying active compounds or compounds that can serve as leads for developing active medicaments for managing metabolic disorders, in particular for treating diabetes, obesity, insulin resistance and/or syndrome X.

In particular, the invention is based on the demonstration and characterization of the role of a specific nuclear receptor, REV-ERB ALPHA, in the mechanisms of adipocyte differentiation, and particularly on the ability of said receptor, when it is overexpressed, to sensitize cells to the action of adipocyte differentiation factors. The invention is also based on the production of specific vectors allowing expression of the REV-ERB ALPHA receptor, and on genetically modified cell lines, particularly pre-adipocytes. The results obtained reveal a modulation of adipocyte differentiation of such lines when they are contacted with agonists or antagonists of receptors directly or indirectly involved in the adipocyte differentiation process.

White adipose tissue is the principal site of energy storage in eukaryotes. Its role is to store triglycerides during periods of abundance and mobilize them when energy supplies diminish. A deregulation of adipocyte activity leads to obesity and its consequences such as non-insulin-dependent diabetes. The adipocytes constituting white adipose tissue are highly specialized cells expressing a defined set of genes characteristic of their differentiation (Fajas et al., Curr. Opin. Cell Biol. 1998, 10: 165-173; Spiegelman, Diabetes 1998, 47: 507-514; Gregoire F., Phys. Rev. 1998, 78: 783-809).

Adipocyte differentiation is a complex process the molecular components of which are becoming more clearly understood (Fajas et al., Curr. Opin. Cell Biol. 1998, 10: 165-173; Spiegelman, Diabetes 1998, 47: 507-514; Gregoire F., Phys. Rev. 1998, 78: 783-809).

Adipocyte differentiation is subjected to a coordinated regulation by a network of several transcription factors. It is initiated by exit from the cell cycle and activation of the factors C/EBP beta, C/EBP delta and ADD1 (SREBP1c), which induce expression of the nuclear receptor activated by "peroxisome proliferators" of the gamma type, hereinbelow named PPAR GAMMA, the principal coordinator of adipocyte differentiation.

The PPAR GAMMA receptor stimulates exit from the cell cycle and expression of genes specific of adipocytes which allow storage of energy. Finally, the C/EBP alpha transcription factor cooperates with the PPAR GAMMA receptor in the final steps of adipocyte differentiation to induce a new set of genes and to maintain expression of said PPAR GAMMA receptor.

The REV-ERB ALPHA receptor is an orphan nuclear receptor the natural or artificial ligands of which are unknown. Its sequence is encoded on the non-coding strand of the gene coding for the thyroid hormone receptor type alpha (Lazar, M. A. et al., Mol. Cell. Biol. 1989, 9(3): 1128-1136; Lazar, M. A. et al., DNA Cell Biol. 1990, 9(2): 77-83; Laudet, V. et al., Nucleic Acid Res. 1991, 19(5): 1105-1012). It acts mainly as a transcription inhibitor. Its expression appears to increase during differentiation of pre-adipocytes to adipocytes and is correlated with the expression of markers of adipocyte differentiation (Chawla, J. Biol. Chem. 1993, 266,12: 16265-16269).

The REV-ERB ALPHA receptor acts as a negative transcriptional regulator (Laudet, V. et al., Curr. Biol. 1995, 5(2): 124-127). It has been shown that the human REV-ERB ALPHA receptor regulates its own expression (Adelmant, G. et al., Proc. Natl. Acad. Sci. USA 1996, 93(8): 3553-3558). REV-ERB ALPHA receptor mRNA is highly expressed in tissues such as adipose tissue, striated muscle, liver and brain tissue and less abundantly in other tissues.

The REV-ERB ALPHA receptor is induced during adipocyte differentiation (Chawla, A. et al., J. Biol. Chem. 1993, 268(22): 16265-16269). However, the molecular mechanism of this regulation remains obscure. It has also been observed that the REV-ERB ALPHA receptor is involved in muscle differentiation (Downes M. et al., Mol. Endocrinol. 1995, 9(12): 1666-1678) and in the regulatory mechanism of lipid metabolism, due to the identification of the rat apoA1 gene (gene encoding apolipoprotein A1) as target gene of the REV-ERB ALPHA receptor in liver (Vu-Dac, N., J. Biol. Chem. 1998, 273: 25713-25720). It has further been suggested that the REV-ERB ALPHA receptor acts as a modulator of thyroid hormone signaling (Lazar M. A., J. Biol. Chem. 1990, 265(22): 12859-12863; Munroe, S. H. et al., J. Biol. Chem. 1991, 266(33): 22803-22086). In fact, the REV-ERB ALPHA receptor binds to the DR4 hormone response element (Spanjaard, R. A. et al., Mol. Endocrinol. 1994, 8(3): 286-295) and inhibits formation of the TR homodimer and TR/RXR heterodimers of TREs (Downes, M. et al., Mol. Endocrinol. 1995, 9: 1666-1678).

So far, the biological role of the REV-ERB ALPHA receptor in adipose tissue and its mechanism of action have not yet been clarified (Chawla, A. et al., J. Biol. Chem. 1993, 268(22): 16265-16269).

The work carried out by the inventors has now elucidated interactions between two receptors, REV-ERB ALPHA and PPAR GAMMA. These studies showed that the PPAR GAMMA receptor activates transcription of the Rev-erb alpha gene via the DR2 response element of the Rev-erb alpha gene promoter (named "Rev-DR2"). The inventors were therefore able to determine that the Rev-erb alpha gene is a target of the PPAR GAMMA receptor, that the REV-ERB ALPHA receptor is a promoter of adipocyte differentiation induced by the PPAR GAMMA receptor, and that it plays a modulating role in adipogenesis.

The inventors have also shown that, in a surprising manner, overexpression of the REV-ERB ALPHA receptor in pre-adipocytes, such as the 3T3-L1 cell line, increases the differentiation of said pre-adipocytes and increases the expression of the PPAR GAMMA receptor in said cells.

In this manner, the inventors have identified regulatory mechanisms between REV-ERB ALPHA receptors and other receptors involved in the adipocyte differentiation program, particularly the PPAR GAMMA receptor. On the basis of this work, they now propose a novel method for screening compounds capable of interacting either with the REV-ERB ALPHA receptor or with said other receptors involved in the adipocyte differentiation program.

Said method is useful for identifying active compounds for treating pathologies linked to metabolic abnormalities involving said receptors, such as adipocyte differentiation, diabetes, obesity, insulin resistance and syndrome X.

It is known that some compounds used for treating disorders linked to abnormalities of adipocyte differentiation, such as diabetes or obesity, exert their action by interacting with the PPAR GAMMA receptor. For example, the thiazolidinediones, also known as glitazones—used to treat insulin resistance—have been identified as ligands and artificial activators of the PPAR GAMMA receptor. Also, fatty acid derivatives have been identified as natural ligands of the PPAR GAMMA receptor. Fibrates are also potent regulators of lipid metabolism which act as activators of the PPAR ALPHA receptor.

The results of in vivo and in vitro studies carried out by the inventors and described herein show that treatment with rosiglitazone (also named BRL49653 or BRL) increases the expression of the mRNA coding for the REV-ERB ALPHA receptor. The glitazones, antidiabetic agents frequently used in the treatment of type 2 diabetes, therefore induce the adipocyte differentiation program via binding and activation of the PPAR GAMMA nuclear receptor.

A first aspect of the invention therefore concerns methods for screening active molecules, in particular molecules having an activity in modulating adipocyte differentiation, based on the use of the REV-ERB ALPHA receptor as molecular target.

Another aspect of the invention relates to genetic constructs, cells and compositions useful for practicing said screening methods, for example pre-adipocyte cells genetically modified to overexpress the REV-ERB ALPHA receptor, and methods for preparing said cells.

A specific aspect of the invention also concerns recombinant viruses (or viral vectors) coding a REV-ERB ALPHA polypeptide.

A further aspect of the invention concerns the use of active compounds for carrying out methods of therapeutic or vaccinal treatment of the human or animal body. In particular, these are compounds capable of interfering with the binding of the PPAR GAMMA receptor to the Rev-DR2 site or, more generally, with the activity or expression of the REV-ERB ALPHA receptor in adipocyte differentiation.

REV-ERB ALPHA Receptor

The invention is based in particular on the identification of the role of the REV-ERB ALPHA receptor in adipocyte differentiation, on the characterization of the mechanisms underlying said role, and on the use of this molecule for a therapeutic purpose.

In the spirit of the invention, the term REV-ERB ALPHA receptor denotes a nuclear receptor comprising the primary amino acid sequence SEQ ID NO: 4, or a fragment or functional variant thereof.

MTTLDSNNNTGGVITYIGSSGSSPSR (séquence SEQ ID NO: 4)

TSPESLYSDNSNGSFQSLTQGCPTYF

PPSPTGSLTQDPARSFGSIPPSLSDD

GSPSSSSSSSSSSSSFYNGSPPGSLQ

VAMEDSSRVSPSKSTSNITKLNGMVL

LCKVCGDVASGFHYGVHACEGCKGFF

-continued

RRSIQQNIQYKRCLKNENCSIVRINR

NRCQQCRFKKCLSVGMSRDAVRFGRI

PKREKQRMLAEMQSAMNLANNQLSSQ

CPLETSPTQHPTPGPMGPSPPPAPVP

SPLVGFSQFPQQLTPPRSPSPEPTVE

DVISQVARAHREIFTYAHDKLGSSPG

NFNANHASGSPPATTPHRWENQGCPP

APNDNNTLAAQRHNEALNGLRQAPSS

YPPTWPPGPAHHSCHQSNSNGHRLCP

THVYAAPEGKAPANSPRQGNSKNVLL

ACPMNMYPHGRSGRTVQEIWEDFSMS

FTPAVREVVEFAKHIPGFRDLSQHDQ

VTLLKAGTFEVLMVRFASLFNVKDQT

VMFLSRTTYSLQELGAMGMGDLLSAM

FDFSEKLNSLALTEEELGLFTAVVLV

SADRSGMENSASVEQLQETLLRALRA

LVLKNRPLETSRFTKLLLKLPDLRTL

NNMHSEKLLSFRVDAQ

The term "fragment" typically designates a polypeptide comprising from 5 to 200 consecutive amino acids of SEQ ID NO: 4, preferably from 5 to 150, even more preferably from 5 to 100. Particular examples of fragments are polypeptides of 5 to 80 amino acids. Preferably, the fragments comprise a functional domain of sequence SEQ ID NO: 4, for example a transcription inhibitor domain and/or a DNA binding domain. The term "functional variant" encompasses natural variants, particularly those resulting from polymorphism(s), splicing(s), interspecies variation(s), and the like. Said term also includes synthetic variants, particularly polypeptides comprising a sequence derived from sequence SEQ ID NO: 4 by one or more mutations, deletions, substitutions and/or additions of one or more residues. In a preferred manner, a synthetic variant shows 75% primary sequence homology with sequence SEQ ID NO: 4, even more preferably, at least 85%. The fragments or variants may further contain added heterologous regions or chemical, enzymatic, immunologic, modifications, etc. For instance, said modifications may facilitate the production or purification of the receptor, improve its stability, increase its activity, etc.

In a preferred embodiment of the invention, the term REV-ERB ALPHA receptor designates a receptor of human origin, particularly a receptor comprising sequence SEQ ID NO: 4 or a fragment thereof.

The term "Rev-erb alpha gene" generally denotes any portion of the genome coding a REV-ERB ALPHA receptor such as defined hereinabove.

The term "Rev-erb alpha genetic construct" or "recombinant nucleic acid coding a REV-ERB ALPHA receptor" generally designates any nucleic acid encoding a REV-ERB ALPHA receptor such as defined hereinabove. It may be a DNA or an RNA, for example a genomic DNA, cDNA, mRNA, synthetic or semi-synthetic DNA. These may be obtained by cloning from libraries or plasmids, or by synthesis, or by any other method known to those skilled in the art.

In a particular embodiment of the invention, the Rev-erb alpha genetic construct is a nucleic acid comprising sequence SEQ ID NO: 3, a fragment thereof, or any sequence hybridizing with the above under conditions of moderate stringency and encoding a REV ERB ALPHA receptor.

Conditions of moderate stringency are described for example in Maniatis et al. The following conditions are given as an example: incubation at 42° C. for 12 hours in a medium containing 50% formamide, 5×SSPE, 5×Denhardt's solution, 0.1% SDS.

Typically, the nucleic acid used for the recombination (recombinant nucleic acid) or genetic construct comprises, in addition to a region coding the REV-ERB ALPHA receptor, one or more transcriptional regulatory regions, typically a transcriptional promoter and/or terminator. Said regulatory regions are selected according to the host cell used. Preferably, they are regulatory regions that function in mammalian

```
     atg acgaccctgg actccaacaa caacacaggt                               (SEQ ID NO: 3)

661 ggcgtcatca cctacattgg ctccagtggc tcctccccaa gccgcaccag ccctgaatcc 721 ctctatagtg acaactccaa tggcagcttc cagtccctga cccaaggctg tcccacctac 781 ttcccaccat cccccactgg ctccctcacc caagacccgg ctcgctcctt tgggagcatt 841 ccacccagcc tgagtgatga cggctcccct tcttcctcat cttcctcgtc gtcatcctcc 901 tcctccttct ataatgggag cccccctggg agtctacaag tggccatgga ggacagcagc 961 cgagtgtccc ccagcaagag caccagcaac atcaccaagc tgaatggcat ggtgttactg 1021 tgtaaagtgt gtggggacgt tgcctcgggc ttccactacg gtgtgcacgc ctgcgagggc 1081 tgcaagggct ttttccgtcg gagcatccag cagaacatcc agtacaaaag gtgtctgaag 1141 aatgagaatt gctccatcgt ccgcatcaat cgcaaccgct gccagcaatg tcgcttcaag 1201 aagtgtctct ctgtgggcat gtctcgagac gctgtgcgtt ttgggcgcat ccccaaacga 1261 gagaagcagc ggatgcttgc tgagatgcag agtgccatga acctggccaa caaccagttg 1321 agcagccagt gcccgctgga gacttcaccc acccagcacc ccaccccagg ccccatgggc 1381 ccctcgccac cccctgctcc ggtcccctca ccctggtgg gcttctccca gtttccacaa 1441 cagctgacgc ctcccagatc cccaagccct gagcccacag tggaggatgt gatatcccag 1501 gtggcccggg cccatcgaga gatcttcacc tacgcccatg acaagctggg cagctcacct 1561 ggcaacttca atgccaacca tgcatcaggt agccctccag ccaccacccc acatcgctgg 1621 gaaaatcagg gctgcccacc tgcccccaat gacaacaaca ccttggctgc ccagcgtcat 1681 aacgaggccc taaatggtct gcgccaggct ccctcctcct accctcccac ctggcctcct 1741 ggccctgcac accacagctg ccaccagtcc aacagcaacg ggcaccgtct atgccccacc 1801 cacgtgtatg cagccccaga aggcaaggca cctgccaaca gtccccggca gggcaactca 1861 aagaatgttc tgctggcatg tcctatgaac atgtacccgc atggacgcag tgggcgaacg 1921 gtgcaggaga tctgggagga tttctccatg agcttcacgc ccgctgtgcg ggaggtggta 1981 gagtttgcca aacacatccc gggcttccgt gacctttctc agcatgacca agtcaccctg 2041 cttaaggctg gcacctttga ggtgctgatg gtgcgctttg cttcgttgtt caacgtgaag 2101 gaccagacag tgatgttcct aagccgcacc acctacagcc tgcaggagct tggtgccatg 2161 ggcatgggag acctgctcag tgccatgttc gacttcagcg agaagctcaa ctccctggcg 2221 cttaccgagg aggagctggg cctcttcacc gcggtggtgc ttgtctctgc agaccgctcg 2281 ggcatggaga attccgcttc ggtggagcag ctccaggaga cgctgctgcg ggctcttcgg 2341 gctctggtgc tgaagaaccg gcccttggag acttcccgct tcaccaagct gctgctcaag 2401 ctgccggacc tgcggaccct gaacaacatg cattccgaga gctgctgtc cttccgggtg 2461 gacgcccagt ga
``` cells. Examples include constitutive or regulated promoters, inducible or not, tissue-selective or ubiquitous, strong or weak, such as for example viral promoters (for example: CMV, LTR, SV40) or from cellular genes. In a particular embodiment, the promoter is the promoter of the Rev-erb alpha gene, comprising for example sequence SEQ ID NO: 1 or a region thereof, for instance a promoter comprising the sequence AAAAGTGTGTCACTGGGGCA (SEQ ID NO: 2).

In a particular embodiment of the invention, the Rev-erb alpha genetic construct is a nucleic acid comprising sequences SEQ ID NO: 3 and SEQ ID NO: 2, a fragment thereof or any sequence hybridizing thereto under conditions of moderate stringency. In a more specific embodiment, the Rev-erb alpha genetic construct is a nucleic acid comprising a sequence coding a polypeptide SEQ ID NO: 4 operationally linked to a transcriptional promoter comprising sequence SEQ ID NO: 1 or a fragment thereof, particularly a transcriptional promoter comprising sequence SEQ ID NO: 2.

Genetically Modified Cells

A particular object of the present invention is based on a cell population comprising a recombinant nucleic acid coding a REV-ERB ALPHA receptor.

The cells may be any cell that can be cultured, preferably mammalian, for example human. They may be primary cells or established cell lines. Preferably, the host cells are pre-adipocyte cells. Said cells are generally defined as cells of the fibroblast type, which are capable of differentiating to adipocytes under suitable culture conditions. More specifically, they are mesodermal cells, incapable of differentiating to chondroblasts, osteoblasts or myoblasts and which, under favorable conditions specific to the cell in question, differentiate to adipocytes and express several differentiation markers characteristic of adipocytes. Examples of pre-adipocyte cells useful for practicing the invention are in particular the cell lines 3T3-L1 (ATCC reference: CL-173), 3T3-F442A (Green H. et al., Cell 1975, 5:19-27), ob17 (Negrel R. et al., Proc. Natl. Acad. Sci. USA, 1978, 75: 6054-6058) or ob1771 (Doglio A. et al., Biochem J., 1986, 238: 123-129).

A particular object of the invention is therefore based on a genetically modified pre-adipocyte cell, wherein it comprises a recombinant nucleic acid coding a REV-ERB ALPHA receptor.

Other examples of cells that may be used within the scope of the invention are prokaryote cells, yeast cells or mammalian cells, particularly embryonic cells or cells such as CHO cells, fibroblasts, Vero cells, and the like.

The recombinant nucleic acid present in the cells enables said cells to express a REV-ERB ALPHA receptor, or to overexpress said receptor, when a basal expression is already present in the cells. Thus, in the case of pre-adipocyte cells, the nucleic acid generally allows the cells to overexpress a REV-ERB ALPHA receptor, that is to say, to produce the receptor at a level higher than that observed in the same cells in the absence of the recombinant nucleic acid construct. The term overexpression generally denotes an expression increased by a factor of 2, more generally by a factor of 3, ideally by a factor of at least 5. The cells are preferably mammalian cells, in particular human cells. It is understood that cells from other species may be used, such as mouse, rat, monkey, hamster cells and the like, for example.

A particular object of the invention concerns a genetically modified cell, particularly pre-adipocyte, overexpressing the REV-ERB ALPHA receptor. The term genetically modified indicates that the cell (or an ancestor thereof) was modified to contain a recombinant nucleic acid coding said receptor.

Typically, the recombinant nucleic acid or genetic construct comprises, in addition to a region coding the REV-ERB ALPHA receptor, one or more transcriptional regulatory regions, typically a transcriptional promoter and/or terminator, such as defined hereinabove. The nucleic acid may be present or incorporated in a plasmid, viral vector, etc. It may be integrated in the cellular genome, or remain in extra-chromosomal form (replicative or not).

The invention also has as its object a method for preparing recombinant cells expressing a REV-ERB ALPHA receptor, particularly genetically modified pre-adipocyte cells overexpressing a REV-ERB ALPHA receptor or a recombinant nucleic acid such as defined hereinabove. The inventive method generally comprises introducing a recombinant nucleic acid such as defined hereinabove coding a REV-ERB ALPHA receptor in a host cell. The host cells may be any cell population such as described hereinabove, preferably a pre-adipocyte, in particular the cell lines 3T3-L1, 3T3-F442A, ob17 or ob1771.

According to a first preferred embodiment of the invention, the recombinant cells are obtained by transfecting host cells with a plasmid vector comprising a Rev-erb alpha genetic construct. In an advantageous manner, the transfection is carried out in the presence of a second genetic construct coding a selection or resistance gene, and the cells are selected for expression of said selection or resistance gene and of the nucleic acid coding REV ERB ALPHA.

In the spirit of the invention, the term "transfection" generally designates any method enabling the transfer of a nucleic acid into a cell. The method may be chemical, physical, biological, and the like. Examples include electroporation, calcium phosphate precipitation, use of agents that facilitate transfection, such as for instance lipids, polymers, peptides, etc., or else the use of physical techniques like "gene gun", the use of projectile, bombardment, and the like.

In a particular embodiment, the method comprises cotransfecting the cells with a plasmid vector comprising said recombinant nucleic acid and with a plasmid vector comprising an antibiotic resistance gene, the cells being selected for their resistance to said antibiotic and for their expression of said recombinant nucleic acid. According to a preferred embodiment of the invention, the recombinant cells are obtained by cotransfecting host cells with a Rev-erb alpha genetic construct overexpressing the REV-ERB ALPHA receptor and with a genetic construct overexpressing an antibiotic resistance gene. The recombinant cells are then selected in the presence of the antibiotic and tested for overexpression of the REV-ERB ALPHA receptor.

According to a particular embodiment of the invention, the antibiotic used is selected in the group consisting of the following substances, which are given as non-limiting examples: neomycin, zeocin, hygromycin, blasticidin, etc.

In a particular embodiment of the method, the nucleic acid is introduced by transfection with a plasmid vector also comprising an antibiotic resistance gene, the cells being selected for their resistance to said antibiotic and for their expression of the recombinant nucleic acid.

According to this variant of the invention, the Rev-erb alpha genetic construct allowing overexpression of the REV-ERB ALPHA receptor also comprises a functional cassette which allows overexpression of an antibiotic resistance gene. The recombinant cells are then selected in the presence of the antibiotic and tested for their overexpression of the REV-ERB ALPHA receptor. In a particular embodiment of the invention, the antibiotic used is selected in the group consisting of the following substances, which are given as non-limiting examples: neomycin, zeocin, hygromycin, blasticidin, etc.

In another embodiment, the nucleic acid is introduced by transfecting with a plasmid vector which additionally comprises an antibiotic resistance gene and a eukaryotic origin of replication, the cells being selected for their resistance to said antibiotic and for their expression of the recombinant nucleic acid. In a more specific embodiment, the Rev-erb alpha genetic construct allowing overexpression of the REV-ERB ALPHA receptor therefore also comprises a functional cassette allowing overexpression of an antibiotic resistance gene and a eukaryotic origin of replication. The recombinant cells are then selected in the presence of the antibiotic and tested for overexpression of the REV-ERB ALPHA receptor. According to a particular embodiment of the invention, the antibiotic used is selected in the group consisting of the following substances, which are given as non-limiting examples: neomycin, zeocin, hygromycin, blasticidin, etc.

According to another preferred embodiment of the invention, the nucleic acid is introduced into the cells by infection with a viral vector comprising said nucleic acid. According to an especially preferred embodiment of the invention, the introduction is accomplished by using a recombinant virus comprising the recombinant nucleic acid coding the REV ERB ALPHA receptor and, as the case may be, the selection or resistance gene ("infection").

Different types of recombinant virus may be used, such as for example retroviruses, adenoviruses, AAV (Adenovirus Associated Virus), herpes viruses, modified baculoviruses, etc. Preferred recombinant viruses are recombinant adenoviruses and retroviruses.

In a preferred embodiment, the recombinant cells (advantageously overexpressing the RNA coding for the REV-ERB ALPHA receptor) are obtained by infecting the host cells, particularly pre-adipocytes, with viral vectors, preferably adenovirus or retrovirus, said vectors containing a nucleic acid coding a REV-ERB ALPHA receptor.

In this respect, another object of the invention is a viral vector comprising a nucleic acid coding a REV-ERB ALPHA receptor. Another object of the invention is a recombinant virus comprising, in its genome, a nucleic acid coding a REV-ERB ALPHA receptor. Preferably, the viral vector is a replication-defective vector, that is to say, incapable of autonomously replicating in a cell. Typically, a viral vector is defective for one or several viral genes essential for replication. In the case of retroviruses, the main viral genes are the gag, pol and env genes. In the case of adenoviruses, the principal genes are contained in the E1A, E1B, E4 and E2 regions. In AAV, the Rep and Cap genomic regions are concerned. The construction of viral vectors, defective for one or several (or all) viral genes and comprising a nucleic acid of interest is known to those skilled in the art. For instance, said methods make use of packaging cell lines and/or vectors or helper virus, as illustrated in the examples.

A particular object of the invention concerns:
- a defective recombinant adenovirus comprising, in its genome, a nucleic acid coding a REV-ERB ALPHA receptor. The adenovirus is preferably a group C adenovirus, particularly Ad5, and/or advantageously comprises a deletion of all or part of the E1A and/or E1B and/or E4 region;
- a defective recombinant retrovirus comprising, in its genome, a nucleic acid coding a REV-ERB ALPHA receptor. The retrovirus is preferably a retrovirus derived from MLV (Mouse Leukemia Virus) or a lentivirus, and/or advantageously bears a deletion of all or part of the gag and/or pol and/or env region.

According to a particular embodiment of the invention, the preparation (e.g., transfection, infection) of cells, particularly of pre-adipocytes, is carried out with a Rev-erb alpha genetic construct which contains, in addition to a region coding the REV-ERB ALPHA receptor, for example SEQ ID NO: 3, one or more transcriptional regulatory regions, typically a transcriptional promoter and/or terminator. According to a preferred embodiment of the invention, these are regulatory regions functional in mammalian cells. Non-limiting examples include constitutive or regulated promoters, inducible or not, tissue-selective or ubiquitous, strong or weak, such as for instance viral promoters (for example: CMV, LTR, SV40) or from cellular genes.

According to a particular embodiment of the invention, the preparation (e.g., transfection) of cells (e.g., pre-adipocytes) is carried out with a Rev-erb alpha genetic construct which comprises, in addition to a region coding the REV-ERB ALPHA receptor, for example SEQ ID NO: 3, the promoter of the Rev-erb alpha gene, for example comprising sequence SEQ ID NO: 1, or comprising a region thereof, for example SEQ ID NO: 2. In another particular embodiment, the preparation is accomplished with a sequence selected from or comprising sequences SEQ ID NO: 1 and SEQ ID NO: 3.

To prepare the recombinant cells of the invention, the host cells may be contacted with the Rev-erb alpha gene or recombinant nucleic acid or vector or virus in any suitable condition, after which the recombinant cells are recovered. Contact may be carried out on any suitable support and in any culture medium suitable to the cell type (for example: DMEM, RPMI, etc.).

In a particular embodiment, after infection or transfection, stable cultured cell lines are selected. The preferred genetically modified cells overexpressing the gene coding the REV-ERB ALPHA receptor are stable lines.

Screening Methods

The present invention also has as object methods for identifying, selecting, characterizing or optimizing compounds capable of modulating adipocyte differentiation. Said methods may be carried out in cellular tests or in vitro, for example by binding tests. Said methods principally use a REV ERB ALPHA receptor (or a corresponding nucleic acid) as molecular target.

In a first embodiment, the invention has as its object a method for identifying, selecting, characterizing or optimizing compounds capable of modulating adipocyte differentiation, wherein (i) a compound to be tested is contacted with cells (preferably pre-adipocytes) such as defined as hereinabove, (ii) adipocyte differentiation of said cells is measured or determined and (iii) preferably, said differentiation is compared with adipocyte differentiation of the same said cells in the absence of said compound to be tested.

The cells are preferably pre-adipocyte cells such as defined hereinabove, more particularly pre-adipocyte cells (over)-expressing the REV-ERB ALPHA receptor.

According to a preferred embodiment of the inventive method, the compound to be tested is contacted with cells (preferably genetically modified cells overexpressing the REV-ERB ALPHA receptor) in the presence or absence of at least one activator of a receptor involved in the adipocyte differentiation program or at least one activator of a gene coding a receptor involved in the adipocyte differentiation program.

In fact, the results presented in the examples show in a surprising manner, that expression of the REV-ERB ALPHA receptor in the recombinant cells of the invention sensitizes pre-adipocytes to the action of adipocyte differentiation factors and promotes the differentiation program. Under these conditions, selection of compounds modulating said differentiation is greatly facilitated.

In a first variant of the invention, one uses at least one activator of a receptor involved in the adipocyte differentiation program, such as for example, and not by way of limitation, an activator of the PPAR GAMMA receptor. For example, the PPAR GAMMA receptor activator is selected in the group consisting of but not limited by: thiazolidinediones (rosiglitazone, troglitazone, englitazone, ciglitazone, pioglitazone, KRP-297), N-(2-benzoylphenyl)-L-tyrosines, 15-deoxy-delta-12,14-prostaglandin J2, etc.

In another variant, one uses at least one activator of a gene of a receptor involved in the adipocyte differentiation program. A non-limiting example is to contact the compound to be tested with genetically modified cells overexpressing the REV-ERB ALPHA receptor in the presence or absence of at least one activator of the PPAR gamma gene. Preferably, the activator of the PPAR gamma gene is selected in the group consisting of: C/EBP beta, C/EBP delta, ADD1 (SREBP1c).

The compound and the activator may be contacted with the cells at the same time, or successively. Typically, the activator is added first, followed by the test compound.

Adipocyte differentiation may be measured by staining the differentiated cells. For example, the stain is selected in the group comprising the stains Oil Red O, Sudan Black. Adipocyte differentiation may also be measured by determining the transport or synthesis of fatty acids.

Adipocyte differentiation may also be measured by determining the expression of at least one marker specific of differentiated adipocytes, preferably a marker selected in the group consisting of: aP2, adipsin and leptin.

The inventive method is noteworthy in that it makes it possible to:
  identify compounds capable of modulating the activity of the REV-ERB ALPHA receptor, such as compounds capable of modulating the expression of the Rev-erb alpha gene or compounds that are agonists or antagonists of the REV-ERB ALPHA receptor. Thus, in particular the inventive method allows identification of compounds capable of increasing adipocyte differentiation and representing activators of Rev-erb alpha gene expression or agonists of the REV-ERB ALPHA receptor.
  indirectly identify, in the absence of PPAR gamma gene activator and PPAR GAMMA receptor activator, compounds capable of increasing adipocyte differentiation which act as PPAR GAMMA receptor agonists.

According to specific embodiments, the inventive method makes it possible to:
  identify compounds capable of decreasing adipocyte differentiation and representing REV-ERB ALPHA receptor antagonists.
  identify compounds capable of increasing adipocyte differentiation representing REV-ERB ALPHA receptor agonists
  identify, in the presence of PPAR gamma gene activator and/or PPAR GAMMA receptor activator, compounds capable of reducing adipocyte differentiation.
  identify compounds which are PPAR GAMMA receptor agonists.

It is understood that a receptor agonist or antagonist is a compound which binds to said receptor and respectively activates or inhibits the activity thereof.

The test compound may be of diverse origin and nature. It may be an isolated compound, biological extracts, organic or inorganic molecules, molecular libraries (synthetic, peptides, nucleic acids, etc.) or microorganisms, etc. The test compound may be contacted with the nucleic acid construct or cells on (or in) any suitable support and in particular on a plate, in a tube or flask, membrane, etc. In general, contact is carried out in a multiwell plate which allows numerous and various tests to be conducted in parallel. Typical supports include microtiter plates and more particularly plates containing 96 or 384 wells (or more). Depending on the support and the nature of the test compound, variable quantities of cells may be used to practice the hereindescribed methods. Classically, $10^3$ to $10^6$ cells are contacted with a type of test compound, in a suitable culture medium, and preferably between $10^4$ and $10^5$ cells. The quantity (or concentration) of test compound may be adjusted by the user according to the type of compound (its toxicity, its ability to penetrate inside cells, etc.), the number of cells, the incubation time, etc. Generally, the cells are exposed to quantities of test compounds ranging from 1 nM to 1 mM. Of course it is possible to test other concentrations without deviating from the invention. Each compound may furthermore be tested at different concentrations, in parallel. Also, different adjuvants and/or vectors and/or agents that facilitate penetration of the compounds into cells may also be used, where necessary. Contact may be maintained for example for several minutes to several hours or days, in particular between 5 and 72 hours, generally between 12 and 48 hours.

According to another embodiment, the inventive method comprises selecting compounds capable of modulating expression of the REV-ERB ALPHA receptor, in particular modulating the effect of the PPAR GAMMA receptor on the Rev-erb alpha gene promoter. In fact, the inventors have now shown that the PPAR GAMMA receptor is responsible for modulating REV-ERB ALPHA receptor expression, and that said modulation involves an interaction between the PPAR GAMMA receptor and the Rev-erb alpha gene promoter, particularly at the Rev-DR2 region (SEQ ID NO: 2).

The invention also concerns a method for identifying, selecting, optimizing or characterizing compounds capable of modulating adipocyte differentiation, wherein it comprises (i) contacting a test compound and a nucleic acid comprising the Rev-DR2 sequence or a functional equivalent thereof, in the presence of the PPAR GAMMA receptor, (ii) verifying binding of the PPAR GAMMA receptor to said nucleic acid and, optionally, (iii) comparing said binding with that observed in the absence of test compound, the test compounds modulating PPAR GAMMA receptor binding being compounds modulating adipocyte differentiation.

Measurement of the eventual binding of the test compound, PPAR GAMMA receptor or a complex formed from the PPAR GAMMA receptor and said test compound to the response element may be carried out by any method known to those skilled in the art, for instance by detecting a signal produced by the response element after said binding. These may be direct or indirect methods, such as those using a reporter gene, binding tests, etc.

Thus, a particular method of the invention comprises contacting a test compound and a nucleic acid comprising the sequence Rev-DR2 (sequence SEQ ID NO: 1 or preferably SEQ ID NO: 2) or a functional equivalent thereof, in the presence of the PPAR GAMMA receptor, and verifying a binding of the PPAR GAMMA receptor to said nucleic acid. In an advantageous manner the binding is compared with that observed in the absence of test compound. In another embodiment, the test compound and the PPAR GAMMA receptor are contacted with a reporter system comprising (i) a transcriptional promoter comprising one or more copies of sequence SEQ ID NO: 1, preferably of sequence SEQ ID NO: 2 or a functional variant thereof and (ii) a reporter gene, and the activity of the test compound is determined by measuring its effect on reporter gene expression induced by the PPAR GAMMA receptor.

A particular object of the invention thus concerns a method for identifying, selecting, optimizing or characterizing compounds capable of modulating adipocyte differentiation, wherein it comprises contacting a test compound and the PPAR GAMMA receptor with a reporter system comprising (i) a transcriptional promoter comprising one or more copies of sequence SEQ ID NO: 1, preferably of sequence SEQ ID NO: 2 or a functional variant thereof and (ii) a reporter gene, and evaluating the activity of the test compound by measuring its effect on reporter gene expression induced by the PPAR GAMMA receptor.

The reporter gene may be placed under the control of any promoter (for example, SEQ ID NO: 1) the sequence of which comprises sequence SEQ ID NO: 2 or a functional variant thereof. Said specific sequence may be present in one or more copies in the promoter (preferably 1 to 10 and even more preferably 1 to 6), upstream or downstream or internally, in the same orientation or in the opposite orientation. In a preferred embodiment of the invention, the reporter gene is placed under the control of a promoter comprising one or more copies of sequence SEQ ID NO: 2. Preferably, it is a promoter whose different activity in the absence and presence of the PPAR GAMMA receptor or a functional equivalent can be detected.

In this respect, the response element of the PPAR GAMMA receptor may be associated with a transcriptional minimal promoter. The minimal promoter is a transcriptional promoter having weak or nonexistent basal activity, and which can be increased in the presence of a transcriptional activator (for example the PPAR GAMMA receptor). A minimal promoter may therefore be a naturally weak promoter in mammalian cells, that is to say, producing a non-toxic and/or insufficient expression to obtain a noticeable biological effect. In an advantageous manner, a minimal promoter is a construct prepared from a native promoter, by deleting region(s) not essential to transcriptional activity. For instance, it is preferably a promoter comprising principally a TATA box, generally less than 160 nucleotides in size, centered around the transcription initiation codon. A minimal promoter may thus be prepared from strong or weak, viral, cellular promoters, such as for instance the herpes virus thymidine kinase (TK) gene promoter, the CMV immediate early promoter, the PGK promoter, the SV40 promoter, and the like.

In a preferred embodiment, the reporter gene is placed under the control of the Rev-erb alpha gene promoter, for example a promoter comprising the non-coding sequence of SEQ ID NO: 1.

Any reporter gene may be used in the inventive screening method. Among such, examples include the chloramphenicol acetyltransferase (CAT) gene, luciferase gene of firefly (Luc) or Renilla (Ren), the secreted alkaline phosphatase (SAP) gene or that of beta-galactosidase (β-Gal). The activity of the proteins encoded by said genes can be readily measured by conventional methods and provides an indirect knowledge of the effect of nuclear receptors on gene expression by measuring the quantity of protein produced and/or their enzymatic activity. The reporter system is advantageously introduced in a cell population, which may be prokaryotic or eukaryotic.

Another object of the invention is the use of a compound identified, selected, characterized or optimized according to a method described hereinabove for preparing a medicament for carrying out a method of therapeutic or vaccinal treatment of the human or animal body, particularly a curative or preventive treatment of metabolic diseases, in particular diabetes, obesity, insulin resistance and syndrome X.

Another object of the invention is based on a method for preparing a medicament comprising (i) a step of selecting a compound capable of modulating adipocyte differentiation such as described hereinabove and (ii) contacting a selected compound, or an analog thereof, with a pharmaceutically acceptable vehicle.

A further object of the invention is a method for preparing a compound active on adipocyte differentiation, comprising (i) a step of selecting a compound capable of modulating adipocyte differentiation such as described hereinabove and (ii) synthesizing a selected compound, or an analog thereof.

Other aspects and advantages of the present invention will become apparent in the examples which follow and in the appended figures, which are given for purposes of illustration and not by way of limitation, in which:

FIG. 1 illustrates the results of Northern blot analyses of mRNA extracted from adipose tissue of rats treated or not with rosiglitazone (BRL):

Adult male rats received either rosiglitazone (10 mg/kg/day) or excipient (1% carboxymethylcellulose) for 14 days. Rats were sacrificed and dissected and total RNA was extracted from epididymal and perirenal adipose tissue. Ten micrograms of mRNA were analyzed by Northern blot using REV-ERB ALPHA receptor cDNA (upper panel) or β-actin cDNA (lower panel) as probes.

FIG. 2 shows rosiglitazone (BRL) induction of REV-ERB ALPHA receptor mRNA expression in 3T3-L1 pre-adipocytes.

3T3-L1 pre-adipocytes were grown to confluence in DMEM medium supplemented with 10% fetal calf serum. When the cells reached confluence, they were transferred to DMEM medium supplemented with 10% fetal calf serum and stimulated with a mixture containing IBMX, dexamethasone, insulin, with or without rosiglitazone (1 μM in water) for 9 days. RNA was isolated and analyzed by Northern blot.

FIG. 3 illustrates rosiglitazone (BRL) induction of activity of the Rev-erb alpha gene promoter and the PPAR GAMMA receptor.

3T3-L1 pre-adipocytes were transfected with a plasmid comprising a 1.7 kb fragment of the Rev-erb alpha gene promoter cloned in front of the luciferase reporter gene and with plasmid pSG5-PPAR gamma expressing the murine PPAR GAMMA receptor or with the corresponding empty pSG5 vector. Cells were treated with rosiglitazone (1 μM) and luciferase activity was measured as previously described.

FIG. 4A shows the effects of the PPAR GAMMA receptor on the activity of a construct containing the promoter of the human REV-ERB ALPHA gene containing a wild type or mutant Rev-DR2 site.

FIG. 4B shows the effects of the PPAR GAMMA receptor on the activity of a construct containing the promoter of the human REV-ERB ALPHA gene containing a wild type or mutant Rev-DR2 site cloned in two copies upstream of the SV40 promoter.

Cos cells were transfected with the indicated reporter constructs and pSG5-PPAR-gamma or pSG5 plasmid. Cells were treated with rosiglitazone (BRL) and luciferase activity was measured.

Figure 5:
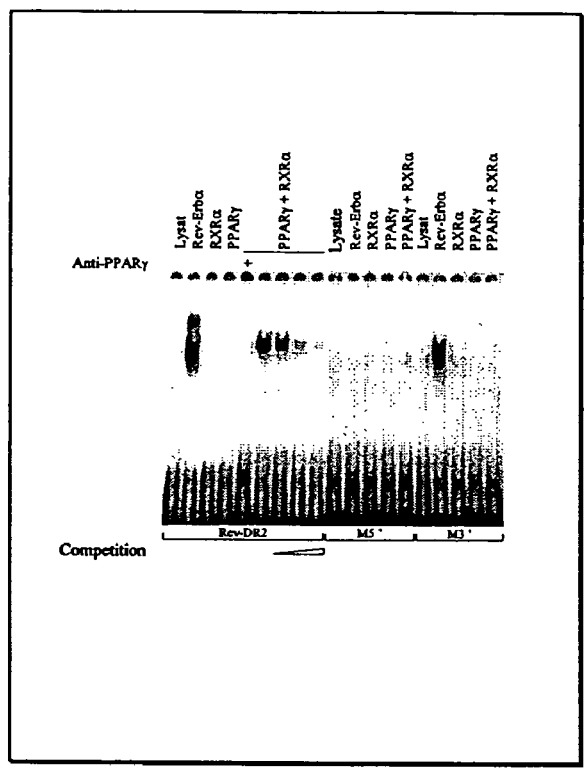

FIG. 5 depicts the electrophoretic gel shift experiments on the PPAR gamma receptor which binds as a heterodimer with the RXR ALPHA nuclear receptor to the Rev-DR2 site of the Rev-erb alpha gene promoter.

The electrophoretic gel shift studies were carried out by using the indicated end-labeled oligonucleotides, in the presence of the murine PPAR GAMMA receptor, murine RXR ALPHA receptor, human REV-ERB ALPHA receptor produced by reticulocyte lysate, or non-programmed lysates (lysate). Binding competition experiments were performed by adding a 0, 10 or 100-fold excess of unlabeled Rev-DR2 oligonucleotide.

Figure 6:
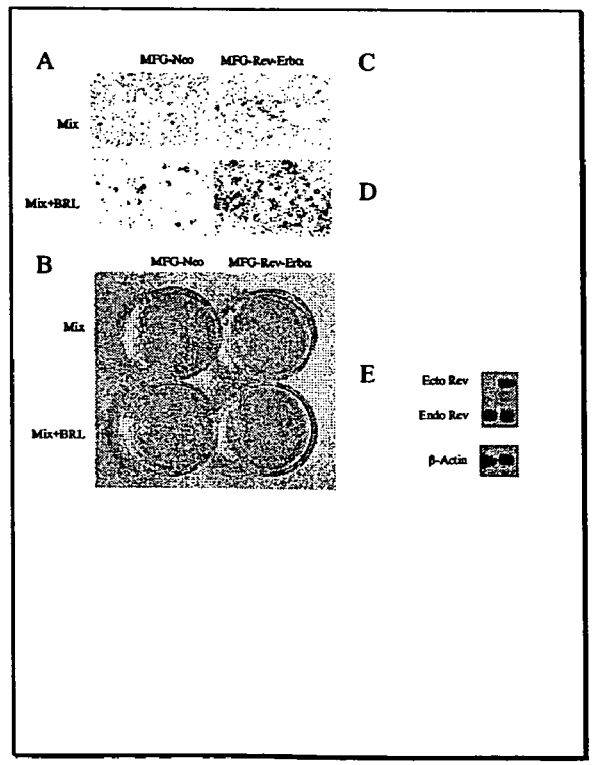

FIG. 6 shows that exogenous expression of the REV-ERB ALPHA receptor stimulates lipid accumulation in 3T3-L1 cells.

3T3-L1 cells were infected with a control retrovirus (MFG-Neo) or with a retrovirus overexpressing the REV-ERB ALPHA receptor (MFG-Rev-erb alpha). The resulting cells were induced to differentiate with or without 1 μM rosiglitazone (BRL) for 8 days. Cells were then fixed and stained with Oil red O.

FIGS. 6A, C and D show the microscopic views of the Oil red O-stained cells.

FIG. 6B shows macroscopic views of plaques stained with Oil red O.

FIG. 6E depicts the exogenous or endogenous expression of REV-ERB ALPHA protein (Ecto-Rev or Endo-Rev) tested by Western blot.

A rabbit anti-REV-ERB ALPHA polyclonal antibody directed against a synthetic peptide (constituted by amino acids 263-365 of the human sequence) was used for the immunocytochemistry and Western blot experiments.

Figure 7:
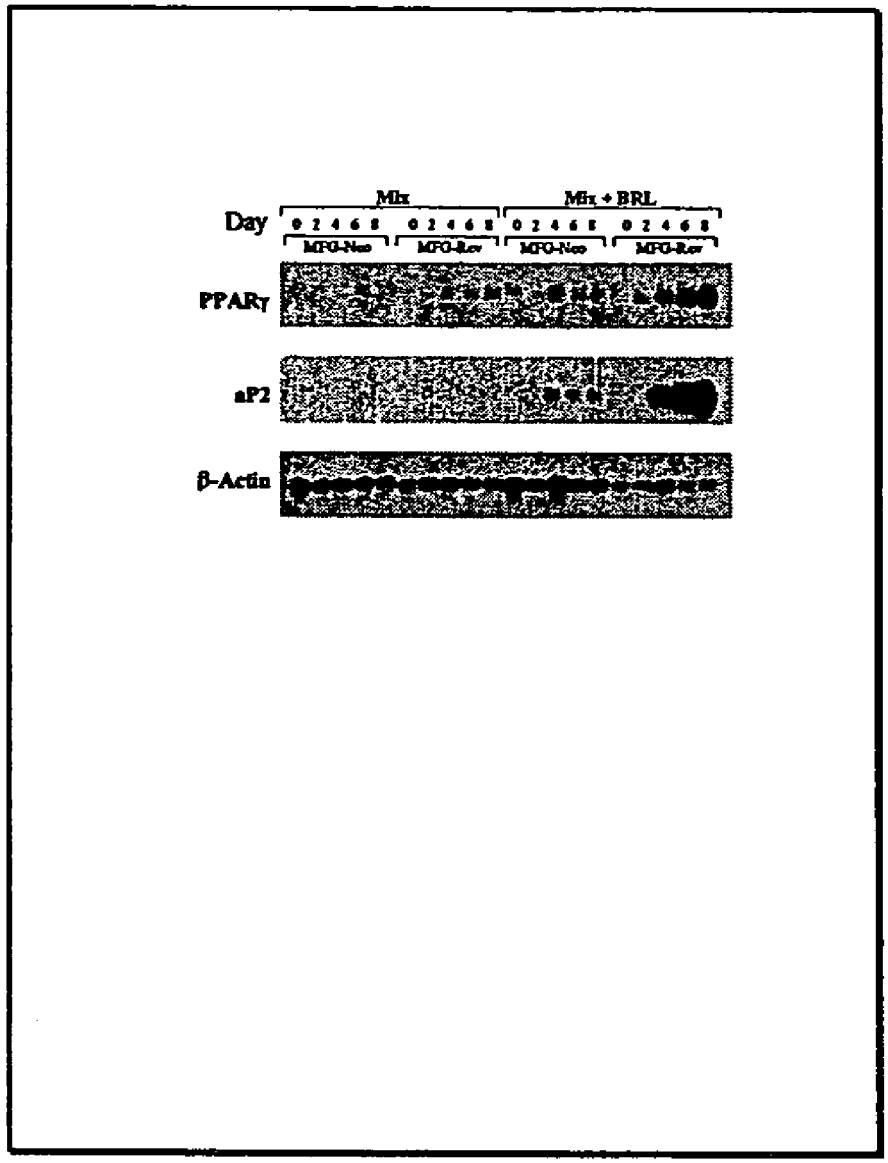

FIG. 7 illustrates the effect of exogenous expression of the REV-ERB ALPHA receptor on expression of the mRNA for the PPAR GAMMA receptor and the aP2 gene used as adipocyte differentiation marker. 3T3-L1 cells were infected with either MFG-Neo or MFG-REV retrovirus and treated for 8 days with a mixture containing IBMX and insulin ("Mix"), with or without 1 μM rosiglitazone. mRNA was then extracted and analyzed by Northern blot using the indicated probes.

Other advantages and features of the invention will become apparent in the following examples which describe the studies carried out by the inventors leading to the design and implementation of the screening method.

1-MATERIALS AND METHODS

Materials

Rosiglitiazone (Ref. BRL49653) was provided by A. Bril (SKB, Rennes, France), GP+E86 cells were from Columbia University (New York, N.Y., USA) and pMFG plasmid from the Massachusetts Institute of Technology (Cambridge, Mass., USA).

Animals

Ten-week-old male Sprague-Dawley rats received rosiglitiazone (10 mg/kg/day) in suspension in 1% carboxymethylcellulose by gavage for 14 days. Control animals received an equivalent volume (5 ml/kg/day) of the carboxymethylcellulose solution. At the end of the experiments, the animals were sacrificed under ether anesthesia. Adipose tissue was immediately removed and frozen in liquid nitrogen.

RNA Analysis

RNA extraction and Northern blot analyses were carried out according to the previously described method (Staels, B. et al., Arteriosclerosis and Thrombosis 1992, 12(3): 286-294) using rat Rev-erb alpha, murine PPAR gamma and murine aP2, chicken beta-actin and human 36B4 cDNA probes.

Transfection Experiments

The constructs comprising fragments of the Rev-erb alpha gene promoter cloned in the promoter-less plasmid pGL2 or in plasmid SV40pGL2 (Promega, Madison, Wis., USA) have been previously described (Adelmant, G. et al., Proc. Natl. Acad. Sci. USA 1996, 93(8): 3553-3558). Human HepG2 hepatoma cells were obtained from the European Collection of cultured animal cells (Porton Down, Salisbury, UK) and 3T3-L1 cells were from the American Type Cell Culture (ATCC). Cells were grown in DMEM medium supplemented with 2 mM glutamine and 10% (vol/vol) fetal calf serum (FCS) in a humidified 5% $CO_2$ atmosphere at 37° C. All transfections were done in triplicate. Luciferase activity was determined on total cell extracts by using a luciferase test system (Promega, Madison, Wis., USA).

In Vitro Translation and Gel Shift Assays.

The pSG5-mPPAR-gamma, pSG5-mRXR-alpha and pSG5-hRev-erb alpha plasmids were transcribed in vitro with T7 polymerase and translated with the rabbit reticulocyte lysate system (Promega, Madison, Wis., USA). Gel shift experiments with REV-ERB ALPHA, PPAR GAMMA and/or RXR ALPHA proteins were carried out as previously described (Gervois, P. et al., Molecular Endocrinology 1999, 13(3): 400-409; Vu-Dac, N. et al., J. Biol. Chem. 1994, 269(49): 31012-31018). For the competition experiments, increasing quantities of the indicated unlabeled probe were added immediately before adding the labeled oligonucleotide. The complexes were resolved in 5% polyacrylamide gels using 0.25×TBE buffer (90 mM borate, 2.5 mM EDTA, pH 8.3) at room temperature. Gels were dried and exposed overnight at −70° C. on Rayon-X film (XOMAT-AR, Eastman Kodak, Rochester, N.Y., USA).

Viral Production and Infection.

GP+E86 virus packaging cells (Markowitz, D. et al., J. Virol. 1988, 62(4): 1120-1124) were grown in DMEM medium (4.5 g/l glucose) supplemented with 10% heat-inactivated calf serum (HyClone, Logan, Utah, USA), 8 μg/ml gentamicin, 50 U/ml penicillin, 50 μg/ml streptomycin, at 37° C. in a 95% humidified air/5% $CO_2$ atmosphere. To generate cell lines constitutively overexpressing the REV-ERB ALPHA receptor, the sequence coding for the REV-ERB ALPHA receptor was inserted upstream of the internal ribosome entry site and the neomycin resistance gene pCITE (Novagen, Madison, Wis., USA) of the retroviral plasmid MFG (Dranoff, G. et al., Proc. Natl. Acac. Sci. USA, 1993, 90(8): 3539-3543) using NcoI-BamHI sites, to produce the pMFG-Rev-erb alpha plasmid.

A similar construct in which the REV-ERB ALPHA receptor sequence was absent was used throughout the study as control (pMFG-Neo).

The bicistronic construct was designed to allow simultaneous expression of the REV-ERB ALPHA receptor and the neomycin resistance gene product in infected cells. To produce recombinant virus, GP+E86 cells (15,000/cm$^2$) were transfected with the MFG plasmid constructs (2 μg)

using lipofectamine (Life Technologies-Invitrogen, Groeningen, The Netherlands) and selecting resistant clones with the geneticin analog G418 (0.8 mg/ml, Life Technologies-Invitrogen, Groeningen, The Netherlands).

3T3-L1 cells were infectd with MFG-Neo or MFG-Rev-erb alpha virus produced by GP+E86 cells as described (Mattot, V. et al., Oncogene 2000, 19(6): 762-772) and selected for resistance to geneticin until establishment of stable lines (approximately 10 days).

Cell Culture and Differentiation.

3T3-L1 cells (obtained from the ATCC) were cultured in DMEM growth medium supplemented with 10% fetal calf serum. Cells were differentiated by the method of Bernlohr et al. (Bernlohr, D.A. et al., Proc. Natl. Acad. Sci. USA 1984, 81(17): 5468-5472).

Cells post-confluent after two days of culture (designated day D0) were transferred to differentiation medium (DMEM, 10% FCS, 1 µM dexamethasone, 10 µg/ml insulin and 0.5 mM 3-methyl-1-isobutylxanthine (IBMX) (Sigma, St Louis, Mo., USA)) for two days. Cells were then grown in post-differentiation medium (DMEM, 10% FCS, insulin) with or without rosiglitazone. The medium was changed every day. Stable 3T3-L1 pre-adipocytes expressing the REV-ERB ALPHA receptor were grown in the same conditions but differentiated without dexamethasone. After the treatment, cells were fixed with 10% formaldehyde in PBS and stained with Oil Red O (Sigma, St Louis, Mo., USA). Alternatively, total RNA was extracted as described earlier.

RESULTS

Activation of the PPAR GAMMA Receptor Increases Expression of the REV-ERB ALPHA Receptor in Rat Adipose Tissue.

Figure 1:
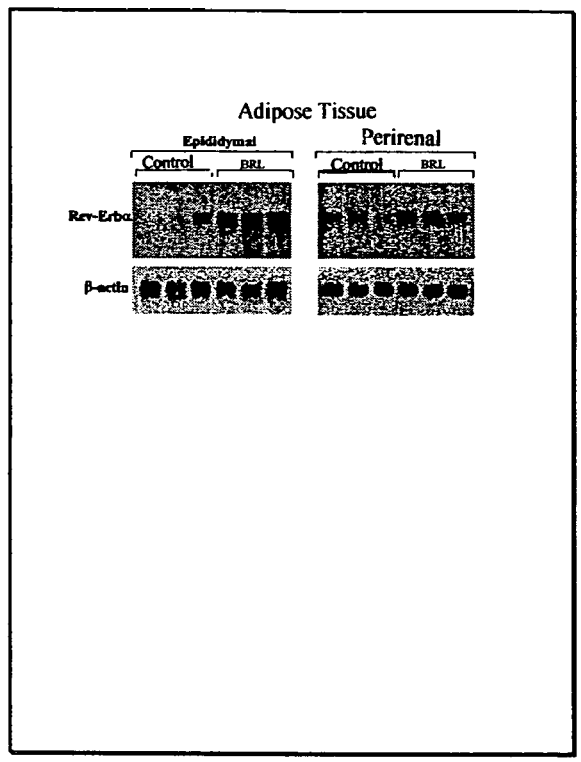

To determine whether activation of the PPAR GAMMA receptor has an effect on REV-ERB ALPHA receptor expression in vivo, rats were treated for 14 days with rosiglitazone (designated BRL), a highly specific, active ligand of the PPAR GAMMA receptor. REV-ERB ALPHA receptor expression was analyzed in epididymal and perirenal adipose tissue by Northern blot. In comparison with the control, treatment with rosiglitazone sharply increased the levels of REV-ERB ALPHA receptor mRNA in the adipose tissues studied (FIG. 1). Levels of beta-actin mRNA used as control were unaffected by the treatment. These experiments show that activation of the PPAR GAMMA receptor by rosiglitazone increases REV-ERB ALPHA receptor expression in adipose tissue.

Activation of the PPAR GAMMA Receptor Induces REV-ERB ALPHA Receptor mRNA in 3T3-L1 Pre-adipocytes.

Figure 2:
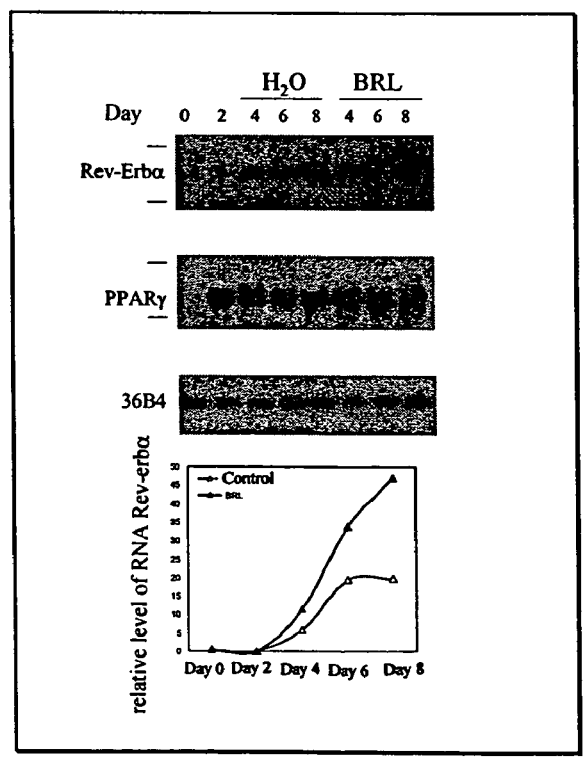

To investigate the molecular mechanism of this induction, the inventors studied the regulation of expression of REV-ERB ALPHA receptor mRNA by rosiglitazone in 3T3-L1 pre-adipocytes (FIG. 2). 3T3-L1 pre-adipocytes were grown to confluence in a medium supplemented with 10% fetal calf serum. Confluent cells were transferred to a medium containing lipid-depleted serum and cells were differentiated with a mixture containing dexamethasone, IBMX, insulin, with or without rosiglitazone (1 µM).

Levels of REV-ERB ALPHA receptor mRNA increased as the pre-adipocytes differentiated to adipocytes. However, compared with the standard differentiation treatment, REV-ERB ALPHA receptor mRNA levels were induced earlier when rosiglitazone was present. Said levels were significantly higher after 9 days in fully differentiated 3T3-L1 adipocytes.

Beta-actin mRNA levels used as control were practically unchanged during adipogenesis and were not affected by treatment with rosiglitazone.

The PPAR GAMMA Receptor Induces REV-ERB ALPHA Receptor Expression at the Transcriptional Level.

To clarify whether induction of REV-ERB ALPHA receptor mRNA takes place at the level of transcription, the inventors tested the effects of overexpression of the PPAR GAMMA receptor and stimulation by rosiglitazone on the transcriptional activity of a construct comprising a luciferase reporter gene under the control of a 1.7 kb fragment of the Rev-erb alpha gene promoter.

3T3-L1 cells were transfected with the construct comprising the luciferase reporter gene under the control of a 1.7 kb fragment of the Rev-erb alpha gene promoter in the presence of a pSG5-PPAR-gamma expression vector enabling expression of the murine PPAR GAMMA receptor, or the corresponding empty vector pSG5, and treated with rosiglitazone or the excipient.

Figure 3:
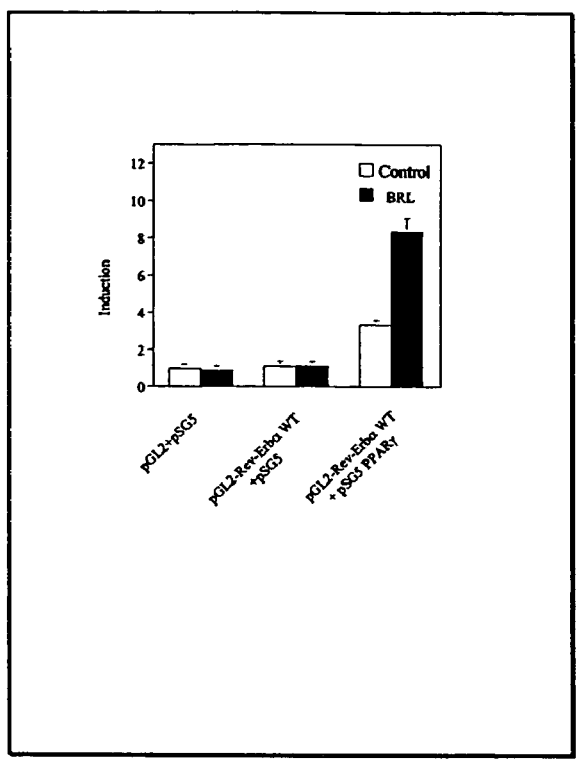

The activity of the Rev-erb alpha gene promoter was induced by overexpression of the PPAR GAMMA receptor, an effect which moreover was amplified in the presence of rosiglitazone (FIG. 3). On the other hand, when the construct comprising the luciferase reporter gene under the control of a 1.7 kb fragment of the Rev-erb alpha gene promoter was transfected alone, no effect was observed. These findings indicate that transcription of the Rev-erb alpha gene is induced by rosiglitazone via activation of the PPAR gamma receptor.

An element named Rev-DR2, showing strong homology with a "DR2" response element of a nuclear receptor, was identified in the Rev-erb alpha gene promoter. It was shown that said REV-ERB ALPHA receptor binds to this site and represses its own transcription via the site (Adelmant, G. et al., Proc. Natl. Acad. Sci. USA 1996, 93(8): 3553-3558). This was also identified as the response element to which the PPAR alpha/RXR ALPHA heterodimer binds to confer a fibrate response to the Rev-erb alpha gene in liver (Gervois et al., Mol. Endocrinol. 1999, 13: 400-409).

Figure 4:
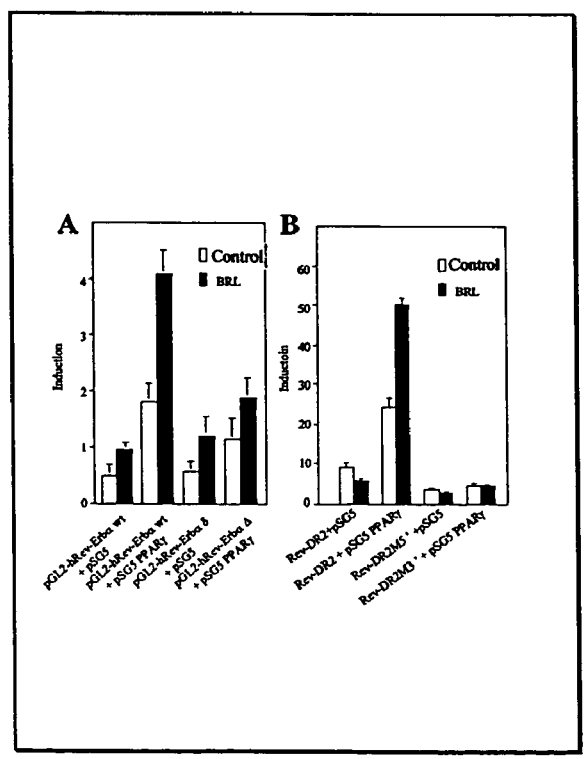
FIG. 4 illustrates the role of the Rev-DR2 site in induction of Rev-erb alpha gene promoter activity by the PPAR GAMMA receptor.

To confirm that the Rev-DR2 site can also function as a response element of the PPAR GAMMA receptor in adipose tissue, the inventors conducted transient transfection experiments using constructs comprising wild-type and truncated versions of the Rev-erb alpha gene promoter named pGL2-hRev-erbαδ and pGL2-hRev-erbαΔ described previously (Adelmant, G. et al., Proc. Natl. Acad. Sci. USA 1996, 93(8): 3553-3558) (FIG. 4). To confirm that the Rev-DR2 site can also function as a response element of the PPAR GAMMA receptor in adipose tissue, the inventors also carried out transient transfection experiments using the previously described constructs (Adelmant, G. et al., Proc. Natl. Acad. Sci. USA 1996, 93(8): 3553-3558) comprising wild-type and mutated versions of the Rev-DR2 site cloned upstream of the SV40 promoter (Rev-DR2, Rev-DR2M5' and Rev-DR2M3') (FIG. 4). Cotransfection of HepG2 cells with a PPAR GAMMA receptor expression vector and a reporter vector comprising two copies of the wild-type Rev-DR2 site cloned upstream of the SV40 promoter and a luciferase reporter gene led to a 2.5-fold greater induction of transcriptional activity as compared to the level observed with the empty pSG5 vector. On the other hand, no effect was seen when the reporter vector comprised two copies of the mutated Rev-DR2 site in either 3' or 5' position. The effect of overexpression of the PPAR GAMMA receptor was amplified in the presence of rosiglitazone. These results clearly demonstrate that the activity of the Rev-erb alpha gene promoter is regulated by the PPAR GAMMA receptor and that this induction is effected through the Rev-DR2 site (FIG. 4).

The PPAR GAMMA Receptor Binds as a Heterodimer with the RXR ALPHA Receptor to the Rev-DR2 Site.

Lastly, binding of the PPAR GAMMA receptor to the Rev-DR2 site was studied. A test to measure electrophoretic mobility (gel shift or electrophoretic mobility shift assay) was carried out using PPAR GAMMA and RXR ALPHA proteins synthesized in vitro. As control, the in vitro-produced REV-ERB ALPHA receptor was shown to bind to the wild-type Rev-DR2 site as both monomer and homodimer (FIG. 5). In contrast, no binding was observed when the Rev-DR2 oligonucleotide bore a mutation on the AGGTCA half-site located 5' (M5') as previously described (Adelmant, G. et al., Proc. Natl. Acad. Sci. USA 1996, 93(8): 3553-3558). Finally, the REV-ERB ALPHA receptor bound as a monomer to the Rev-DR2 site bearing a mutation on the AGGTCA half-site located 3' (M3') as previously described (Adelmant, G. et al., Proc. Natl. Acad. Sci. USA 1996, 93(8): 3553-3558). The RXR ALPHA or PPAR GAMMA receptors alone did not bind to any of the oligonucleotides indicating that PPAR GAMMA and RXR ALPHA cannot bind in monomeric form. Binding to the Rev-DR2 site was seen when the PPAR GAMMA receptor was incubated with the RXR ALPHA receptor. Binding was specific because it could be competed with an excess of unlabeled oligonucleotide. In contrast, the PPAR GAMMA/RXR ALPHA complex did not bind to the mutant Rev-DR2 site (M5' or M3'). These binding studies show that PPAR GAMMA binds as a heterodimer with RXR ALPHA to the intact Rev-DR2 site of the Rev-erb alpha gene promoter.

The REV-ERB ALPHA Receptor Increases the Adipogenic Activity of the PPAR GAMMA Receptor.

To directly confirm the participation of the REV-ERB ALPHA receptor in adipogenesis, the entire cDNA encoding the REV-ERB ALPHA receptor was cloned in a retroviral vector. 3T3-L1 pre-adipocytes were then infected with the resulting virus. Stable cell lines established by antibiotic selection with G418 (neomycin) after infection with either MFG-Neo virus (negative control) or MFG-Rev-erb alpha virus, were grown to confluence and then treated with a differentiation medium (designated Mix) containing IBMX, insulin with or without rosiglitazone (BRL) (1 µM). Endogenous or viral-induced expression of REV-ERB ALPHA was checked by immunocytochemical analysis or by Western blot (FIG. 6E). Cells infected with MFG-Neo expressed high levels of REV-ERB ALPHA receptor in comparison with MFG-Neo-infected control cells.

In the absence of rosiglitazone, exogenous expression of the REV-ERB ALPHA receptor induced only a weak morphological differentiation of the pre-adipocytes. In the presence of rosiglitazone (1 µM), there was an increase in pre-adipocyte differentiation and in lipid accumulation in cells expressing the REV-ERB ALPHA receptor as compared with control cells. In fact, after fixation and staining with Oil red O, a weak accumulation of lipids was observed in the absence of rosiglitazone, but high lipid accumulation was seen in cells expressing the REV-ERB ALPHA receptor treated with rosiglitazone for 8 days (FIGS. 6A-6D). To obtain the same result with rosiglitazone alone without hormonal stimulation, the cells had to be differentiated for 16 days (data not shown).

These morphological changes occurred in parallel to a similar variation in mRNA levels of adipocyte-specific markers. Northern blot analyses showed a weak but significant expression of the PPAR GAMMA receptor and aP2 in cells expressing the REV-ERB ALPHA receptor (FIG. 7).

In a surprising manner, endogenous levels of the REV-ERB ALPHA receptor were perturbed in cells overexpressing the REV-ERB ALPHA receptor. aP2 and PPAR GAMMA receptor mRNA levels were high in cells expressing the REV-ERB ALPHA receptor treated with a rosiglitazone mixture after only four days of differentiation (FIG. 7), or with rosiglitazone alone (FIG. 7). This phenomenon was not observed until 8-12 days in control cells. These findings show that exogenous expression of the REV-ERB ALPHA receptor has a weak effect without hormonal stimulation and amplifies induction of adipogenesis by PPAR GAMMA ligand activation.

It is in this manner that the use of the pre-adipocyte cell line of the invention, overexpressing the REV-ERB ALPHA receptor, enabled identification of the Rev-erb alpha gene as a novel target gene for the PPAR GAMMA receptor in the adipogenic transcription factor cascade. This observation of the active role of the REV-ERB ALPHA receptor in the adipocyte differentiation process allowed the inventors to develop a novel screening method to identify active compounds involved in adipocyte modulation.

The invention claimed is:

1. A method for identifying compounds that modulates adipocyte differentiation, wherein (i) a test compound is contacted with a population of genetically modified pre-adipocyte cells, wherein said genetic modification comprises introduction into said cell a recombinant nucleic acid coding a REV-ERB ALPHA receptor and (ii) adipocyte differentiation of said cells is measured or determined and is compared with adipocyte differentiation of said same pre-adipocyte cells in the absence of said test compound, allowing identification of compounds that modulate adipocyte differentiation, and wherein said REV-ERB ALPHA receptor comprises SEQ ID NO:4.

2. A method according to claim 1, wherein the test compound is contacted with cells overexpressing the REV-ERB ALPHA receptor in the presence of at least one activator of the PPAR GAMMA receptor.

3. A method according to claim 1, wherein the test compound is contacted with cells overexpressing the REV-ERB ALPHA receptor in the presence of at least one activator of a receptor involved in the adipocyte differentiation process, which is selected in the group consisting of thiazolidinediones, N-(2-benzoylphenyl)-L-tyrosines and 15-deoxy-delta 12,14-prostaglandin J2.

4. A method according to claim 1, wherein the test compound is contacted with cells overexpressing the REV-ERB ALPHA receptor in the presence of at least one activator of a receptor involved in the adipocyte differentiation process, which is selected in the group consisting of rosiglitazone, troglitazone, englitazone, ciglitazone, pioglitazone, KRP-297.

5. A method according to claim 1, wherein the recombinant nucleic acid comprises sequence SEQ ID NO: 3.

6. A method according to claim 1, wherein the recombinant nucleic acid further comprises sequence SEQ ID NO: 1 or SEQ ID NO: 2.

7. A method according to claim 1, wherein the recombinant nucleic acid is incorporated in a plasmid vector.

8. A method according to claim 1, wherein the recombinant nucleic acid is incorporated in a viral vector.

9. A method according to claim 1, wherein the recombinant nucleic acid is integrated in the cellular genome.

10. A method according to claim 1, wherein adipocyte differentiation is measured (i) by staining the differentiated cells, (ii) by determining fatty acid transport or synthesis, or (iii) by determining the expression of at least one marker specific of differentiated adipocytes.

11. A genetically modified pre-adipocyte cell, wherein said genetic modification comprises introduction into said cell a recombinant nucleic acid coding a REV-ERB ALPHA receptor, said recombinant nucleic acid farther comprising sequence SEQ ID NO: 1 or SEQ ID NO: 2 said REV-ERB ALPHA comprising sequence SEQ ID NO:4.

12. A cell according to claim 11, wherein the recombinant nucleic acid comprises sequence SEQ ID NO: 3.

13. A cell according to claim 11, wherein the recombinant nucleic acid is incorporated in a plasmid vector.

14. A cell according to claim 11, wherein the recombinant nucleic acid is incorporated in a viral vector.

15. A cell according to claim 11, wherein the recombinant nucleic acid is integrated in the cellular genome.

16. A method for preparing a pre-adipocyte cell according to claim 11, wherein a recombinant nucleic acid coding a REVERB ALPHA comprising sequence SEQ ID NO:4 and further comprising one or more transcriptional regulatory regions is introduced into a pre-adipocyte cell.

17. A method according to claim 16, wherein the pre-adipocyte cells are selected from among the cell lines 3T3-L1, 3T3-F442A, ob17 and ob1771.

18. A method according to claim 16, wherein the nucleic acid is introduced by transfection with a plasmid vector.

19. A method according to claim 16, comprising cotransfecting the cells with a plasmid vector comprising said recombinant nucleic acid and a plasmid vector comprising an antibiotic resistance gene, and wherein the cells are selected for their resistance to said antibiotic and for their expression of said recombinant nucleic acid.

20. A method according to claim 16, wherein the nucleic acid is introduced by transfection with a plasmid vector additionally comprising an antibiotic resistance gene and a eukaryotic origin of replication, and wherein the cells are selected for their resistance to said antibiotic and for their expression of said recombinant nucleic acid.

21. A method according to claim 16, wherein the nucleic acid is introduced by infection with a viral vector.

22. A method according to claim 16, wherein the nucleic acid is introduced by infection with a recombinant adenovirus or retrovirus.

23. A method according to claim 16, wherein the recombinant nucleic acid comprises SEQ ID No: 3.

24. A method according to claim 16, wherein the recombinant nucleic acid additionally comprises one or more transcriptional regulatory regions, typically a transcriptional promoter and/or terminator.

25. A method according to claim 16, wherein one transcriptional regulatory region of the recombinant nucleic acid comprises sequence SEQ ID NO: 1 or SEQ ID NO:2.

26. A method according to claim 16, wherein, after infection or transfection, stable pre-adipocyte cell lines in culture are selected.

* * * * *

SEQUENCE LISTING

```
<160> NUMBER OF SEQ ID NOS: 4

<210> SEQ ID NO 1
<211> LENGTH: 1999
<212> TYPE: DNA
<213> ORGANISM: Homo sapiens

<400> SEQUENCE: 1
gaattcatgc tgcctgtgga gaagggcttc ctatgtgaag aaaaccctct ctagaagcac      60
tgggactggg gaggaattag cgggagcagc aggtggctca ggctccctct cccttcgctg     120
cctaagaagc ttccatcccc tccatgaccc aagccctcta acatgataga tctcctctac     180
ttgagatctg ttattactca tgggacagtt gctgctctga agcgaaatac tggctgtttt     240
ttgtttgttt gttttggaga cagagtctca ctctatcccc agggcggagt gcaatggcga     300
```

-continued

```
tctcggctca ctgcaacctc cacctcccgg gttctagcga ttctcctgcc tcagcctcct      360
gactagctgg gattacaggc acccaccacc acatccggct aattttttgta tttttagtag     420 agacgtggtt tcaccgtgtt ggtcaggctg gtctcaaact cctgacctca ggtgatcaac     480
ccacctcagc ctcacaaagt gctgggatta caggcatgag ccaaagcacc cggcaatgct     540
ggctgtttct aacccctgtt cagtatttca cttgtacatc tacccacctt cccattcggg     600
gtgggcagat gaaactagca atggacgtct gaccttgggt cggtcacttc tcctaagctt     660
cctgttcccc actagtaaaa agagggaggc ttaagatgat ctacatgttc ccctctgagt     720
agtaatcttg tgtggaattc atattttatc ctccagcacc gaggggcagg ggtgtcactc     780
tgcccccacc ccctgcctca cctcttcccc attactttag gacctcaaag cactttcact     840
attagttccc ctctgttgtc ctttttattt cccagacaaa gggaaatgac tcaccccaaa     900
gtcaactgga gtgggtggaa tggtgtcaat acaagcaaac agggagtccc tacagacatc     960
cctacctctg tgggaactcc ttcccctgga ggtgttctcc ctaaggcgag tagaagggaa     1020
agggggtcac atttcctttc cttctctgga ctttgccctg aagcagaggg cagcctaagc     1080
tcctgactcc agggaaatct ccctccccgg cttctctctc tcccggtcac cagtaacctc     1140
aggacgaggt cagtcctgca atcacgtgaa gccctcacgt ttgcaaggtt tgcagaaagg     1200
gcctcttagc tttgatctcc cagacagcaa acaagcttgc cagtccctcc ccagaaattc     1260
acatgcccct gccatacagg ctttctaaac acgccaccct gactcttcag cgcaccccac     1320
cccaccccac tctcagctcc tcccaggtcc cggcaagcgc tttgccaggc agaaagggga     1380
aaggcacgca gtccgcccac tttgtcggtg gactacaaat cccgacagtc ttgtcgttgc     1440
gcaggcgcgc aagagctcaa cgtgccggct gttggaaaag tgtgtcactg ggcaccgag     1500 gcgctccctg ggatcacatg gtacctgctc cagtgccgcg tgcggcccgg gaaccctggg     1560
ctgctggcgc ctgcgcagag ccctctgtcc caggaaagg ctcgggcaaa aggcggctga     1620
gattggcaga gtgaaatatt actgccgagg gaacgtagca gggcacacgt ctcgcctctt     1680
tgcgactcgg tgccccgttt ctccccatca cctacttact tcctggttgc aacctctctt     1740
cctctgggac ttttgcaccg ggagctccag attcgctacc ccgcagcgct gcggagccgg     1800
caggcagagg caccccgtac actgcagaga cccgaccctc cttgctacct tctagccaga    1860
actactgcag gctgattccc cctacacact ctctctgctc ttcccatgca aagcagaact     1920
ccgttgcctc aacgtccaac ccttctgcag ggctgcagtc cggccacccc aagaccttgc     1980
tgcagggtgc ttcggatcc                                                  1999
```

<210> SEQ ID NO 2
<211> LENGTH: 20
<212> TYPE: DNA
<213> ORGANISM: artificial sequence
<220> FEATURE:
<223> OTHER INFORMATION: Description of the artificial sequence: Rev-DR2

<400> SEQUENCE: 2

```
aaaagtgtgt cactggggca                                                  20
```

<210> SEQ ID NO 3
<211> LENGTH: 1845
<212> TYPE: DNA
<213> ORGANISM: Homo sapiens
<220> FEATURE:
<221> NAME/KEY: CDS
<222> LOCATION: (1)..(1845)
<223> OTHER INFORMATION: REV ERB ALPHA

<400> SEQUENCE: 3

```
atg acg acc ctg gac tcc aac aac aac aca ggt ggc gtc atc acc tac      48
Met Thr Thr Leu Asp Ser Asn Asn Asn Thr Gly Gly Val Ile Thr Tyr
 1               5                  10                  15 att ggc tcc agt ggc tcc tcc cca agc cgc acc agc cct gaa tcc ctc      96
Ile Gly Ser Ser Gly Ser Ser Pro Ser Arg Thr Ser Pro Glu Ser Leu
                20                  25                  30 tat agt gac aac tcc aat ggc agc ttc cag tcc ctg acc caa ggc tgt     144
Tyr Ser Asp Asn Ser Asn Gly Ser Phe Gln Ser Leu Thr Gln Gly Cys
            35                  40                  45 ccc acc tac ttc cca cca tcc ccc act ggc tcc ctc acc caa gac ccg     192
Pro Thr Tyr Phe Pro Pro Ser Pro Thr Gly Ser Leu Thr Gln Asp Pro
        50                  55                  60 gct cgc tcc ttt ggg agc att cca ccc agc ctg agt gat gac ggc tcc     240
Ala Arg Ser Phe Gly Ser Ile Pro Pro Ser Leu Ser Asp Asp Gly Ser
 65                  70                  75                  80 cct tct tcc tca tct tcc tcg tcg tca tcc tcc tcc tcc ttc tat aat     288
Pro Ser Ser Ser Ser Ser Ser Ser Ser Ser Ser Ser Ser Phe Tyr Asn
                 85                  90                  95 ggg agc ccc cct ggg agt cta caa gtg gcc atg gag gac agc agc cga     336
Gly Ser Pro Pro Gly Ser Leu Gln Val Ala Met Glu Asp Ser Ser Arg
            100                 105                 110 gtg tcc ccc agc aag agc acc agc aac atc acc aag ctg aat ggc atg     384
Val Ser Pro Ser Lys Ser Thr Ser Asn Ile Thr Lys Leu Asn Gly Met
        115                 120                 125 gtg tta ctg tgt aaa gtg tgt ggg gac gtt gcc tcg ggc ttc cac tac     432
Val Leu Leu Cys Lys Val Cys Gly Asp Val Ala Ser Gly Phe His Tyr
130                 135                 140 ggt gtg cac gcc tgc gag ggc tgc aag ggc ttt ttc cgt cgg agc atc     480
Gly Val His Ala Cys Glu Gly Cys Lys Gly Phe Phe Arg Arg Ser Ile
145                 150                 155                 160 cag cag aac atc cag tac aaa agg tgt ctg aag aat gag aat tgc tcc     528
Gln Gln Asn Ile Gln Tyr Lys Arg Cys Leu Lys Asn Glu Asn Cys Ser
                165                 170                 175 atc gtc cgc atc aat cgc aac cgc tgc cag caa tgt cgc ttc aag aag     576
Ile Val Arg Ile Asn Arg Asn Arg Cys Gln Gln Cys Arg Phe Lys Lys
            180                 185                 190 tgt ctc tct gtg ggc atg tct cga gac gct gtg cgt ttt ggg cgc atc     624
Cys Leu Ser Val Gly Met Ser Arg Asp Ala Val Arg Phe Gly Arg Ile
        195                 200                 205 ccc aaa cga gag aag cag cgg atg ctt gct gag atg cag agt gcc atg     672
Pro Lys Arg Glu Lys Gln Arg Met Leu Ala Glu Met Gln Ser Ala Met
210                 215                 220 aac ctg gcc aac aac cag ttg agc agc cag tgc ccg ctg gag act tca     720
Asn Leu Ala Asn Asn Gln Leu Ser Ser Gln Cys Pro Leu Glu Thr Ser
225                 230                 235                 240 ccc acc cag cac ccc acc cca ggc ccc atg ggc ccc tcg cca ccc cct     768
Pro Thr Gln His Pro Thr Pro Gly Pro Met Gly Pro Ser Pro Pro Pro
                245                 250                 255 gct ccg gtc ccc tca ccc ctg gtg ggc ttc tcc cag ttt cca caa cag     816
Ala Pro Val Pro Ser Pro Leu Val Gly Phe Ser Gln Phe Pro Gln Gln
            260                 265                 270 ctg acg cct ccc aga tcc cca agc cct gag ccc aca gtg gag gat gtg     864
Leu Thr Pro Pro Arg Ser Pro Ser Pro Glu Pro Thr Val Glu Asp Val
        275                 280                 285 ata tcc cag gtg gcc cgg gcc cat cga gag atc ttc acc tac gcc cat     912
Ile Ser Gln Val Ala Arg Ala His Arg Glu Ile Phe Thr Tyr Ala His
290                 295                 300
```

-continued

| | | |
|---|---|---|
| gac aag ctg ggc agc tca cct ggc aac ttc aat gcc aac cat gca tca<br>Asp Lys Leu Gly Ser Ser Pro Gly Asn Phe Asn Ala Asn His Ala Ser<br>305                              310                          315                     320 | 960 |
| ggt agc cct cca gcc acc acc cca cat cgc tgg gaa aat cag ggc tgc<br>Gly Ser Pro Pro Ala Thr Thr Pro His Arg Trp Glu Asn Gln Gly Cys<br>                       325                          330                       335 | 1008 |
| cca cct gcc ccc aat gac aac aac acc ttg gct gcc cag cgt cat aac<br>Pro Pro Ala Pro Asn Asp Asn Asn Thr Leu Ala Ala Gln Arg His Asn<br>                  340                          345                       350 | 1056 |
| gag gcc cta aat ggt ctg cgc cag gct ccc tcc tcc tac cct ccc acc<br>Glu Ala Leu Asn Gly Leu Arg Gln Ala Pro Ser Ser Tyr Pro Pro Thr<br>355                             360                          365 | 1104 |
| tgg cct cct ggc cct gca cac cac agc tgc cac cag tcc aac agc aac<br>Trp Pro Pro Gly Pro Ala His His Ser Cys His Gln Ser Asn Ser Asn<br>       370                           375                       380 | 1152 |
| ggg cac cgt cta tgc ccc acc cac gtg tat gca gcc cca gaa ggc aag<br>Gly His Arg Leu Cys Pro Thr His Val Tyr Ala Ala Pro Glu Gly Lys<br>385                             390                       395                   400 | 1200 |
| gca cct gcc aac agt ccc cgg cag ggc aac tca aag aat gtt ctg ctg<br>Ala Pro Ala Asn Ser Pro Arg Gln Gly Asn Ser Lys Asn Val Leu Leu<br>                  405                          410                       415 | 1248 |
| gca tgt cct atg aac atg tac ccg cat gga cgc agt ggg cga acg gtg<br>Ala Cys Pro Met Asn Met Tyr Pro His Gly Arg Ser Gly Arg Thr Val<br>                       420                          425                       430 | 1296 |
| cag gag atc tgg gag gat ttc tcc atg agc ttc acg ccc gct gtg cgg<br>Gln Glu Ile Trp Glu Asp Phe Ser Met Ser Phe Thr Pro Ala Val Arg<br>                       435                          440                       445 | 1344 |
| gag gtg gta gag ttt gcc aaa cac atc ccg ggc ttc cgt gac ctt tct<br>Glu Val Val Glu Phe Ala Lys His Ile Pro Gly Phe Arg Asp Leu Ser<br>       450                           455                       460 | 1392 |
| cag cat gac caa gtc acc ctg ctt aag gct ggc acc ttt gag gtg ctg<br>Gln His Asp Gln Val Thr Leu Leu Lys Ala Gly Thr Phe Glu Val Leu<br>465                             470                       475                   480 | 1440 |
| atg gtg cgc ttt gct tcg ttg ttc aac gtg aag gac cag aca gtg atg<br>Met Val Arg Phe Ala Ser Leu Phe Asn Val Lys Asp Gln Thr Val Met<br>                  485                          490                       495 | 1488 |
| ttc cta agc cgc acc acc tac agc ctg cag gag ctt ggt gcc atg ggc<br>Phe Leu Ser Arg Thr Thr Tyr Ser Leu Gln Glu Leu Gly Ala Met Gly<br>                    500                          505                       510 | 1536 |
| atg gga gac ctg ctc agt gcc atg ttc gac ttc agc gag aag ctc aac<br>Met Gly Asp Leu Leu Ser Ala Met Phe Asp Phe Ser Glu Lys Leu Asn<br>                 515                          520                       525 | 1584 |
| tcc ctg gcg ctt acc gag gag gag ctg ggc ctc ttc acc gcg gtg gtg<br>Ser Leu Ala Leu Thr Glu Glu Glu Leu Gly Leu Phe Thr Ala Val Val<br>       530                           535                       540 | 1632 |
| ctt gtc tct gca gac cgc tcg ggc atg gag aat tcc gct tcg gtg gag<br>Leu Val Ser Ala Asp Arg Ser Gly Met Glu Asn Ser Ala Ser Val Glu<br>545                             550                       555                   560 | 1680 |
| cag ctc cag gag acg ctg ctg cgg gct ctt cgg gct ctg gtg ctg aag<br>Gln Leu Gln Glu Thr Leu Leu Arg Ala Leu Arg Ala Leu Val Leu Lys<br>                       565                          570                       575 | 1728 |
| aac cgg ccc ttg gag act tcc cgc ttc acc aag ctg ctc ctc aag ctg<br>Asn Arg Pro Leu Glu Thr Ser Arg Phe Thr Lys Leu Leu Leu Lys Leu<br>                  580                          585                       590 | 1776 |
| ccg gac ctg cgg acc ctg aac aac atg cat tcc gag aag ctg ctg tcc<br>Pro Asp Leu Arg Thr Leu Asn Asn Met His Ser Glu Lys Leu Leu Ser<br>       595                           600                       605 | 1824 |
| ttc cgg gtg gac gcc cag tga<br>Phe Arg Val Asp Ala Gln<br>       610 | 1845 |

```
<210> SEQ ID NO 4
<211> LENGTH: 614
<212> TYPE: PRT
<213> ORGANISM: Homo sapiens

<400> SEQUENCE: 4

Met Thr Thr Leu Asp Ser Asn Asn Thr Gly Gly Val Ile Thr Tyr
 1               5                  10                  15

Ile Gly Ser Ser Gly Ser Ser Pro Ser Arg Thr Ser Pro Glu Ser Leu
                20                  25                  30

Tyr Ser Asp Asn Ser Asn Gly Ser Phe Gln Ser Leu Thr Gln Gly Cys
            35                  40                  45

Pro Thr Tyr Phe Pro Pro Ser Pro Thr Gly Ser Leu Thr Gln Asp Pro
    50                  55                  60

Ala Arg Ser Phe Gly Ser Ile Pro Pro Ser Leu Ser Asp Asp Gly Ser
65                  70                  75                  80

Pro Ser Ser Ser Ser Ser Ser Ser Ser Ser Ser Ser Phe Tyr Asn
                85                  90                  95

Gly Ser Pro Pro Gly Ser Leu Gln Val Ala Met Glu Asp Ser Ser Arg
                100                 105                 110

Val Ser Pro Ser Lys Ser Thr Ser Asn Ile Thr Lys Leu Asn Gly Met
            115                 120                 125

Val Leu Leu Cys Lys Val Cys Gly Asp Val Ala Ser Gly Phe His Tyr
    130                 135                 140

Gly Val His Ala Cys Glu Gly Cys Lys Gly Phe Phe Arg Arg Ser Ile
145                 150                 155                 160

Gln Gln Asn Ile Gln Tyr Lys Arg Cys Leu Lys Asn Glu Asn Cys Ser
                165                 170                 175

Ile Val Arg Ile Asn Arg Asn Arg Cys Gln Gln Cys Arg Phe Lys Lys
            180                 185                 190

Cys Leu Ser Val Gly Met Ser Arg Asp Ala Val Arg Phe Gly Arg Ile
    195                 200                 205

Pro Lys Arg Glu Lys Gln Arg Met Leu Ala Glu Met Gln Ser Ala Met
210                 215                 220

Asn Leu Ala Asn Asn Gln Leu Ser Ser Gln Cys Pro Leu Glu Thr Ser
225                 230                 235                 240

Pro Thr Gln His Pro Thr Pro Gly Pro Met Gly Pro Ser Pro Pro Pro
                245                 250                 255

Ala Pro Val Pro Ser Pro Leu Val Gly Phe Ser Gln Phe Pro Gln Gln
            260                 265                 270

Leu Thr Pro Pro Arg Ser Pro Ser Pro Glu Pro Thr Val Glu Asp Val
    275                 280                 285

Ile Ser Gln Val Ala Arg Ala His Arg Glu Ile Phe Thr Tyr Ala His
    290                 295                 300

Asp Lys Leu Gly Ser Ser Pro Gly Asn Phe Asn Ala Asn His Ala Ser
305                 310                 315                 320

Gly Ser Pro Pro Ala Thr Thr Pro His Arg Trp Glu Asn Gln Gly Cys
                325                 330                 335

Pro Pro Ala Pro Asn Asp Asn Asn Thr Leu Ala Ala Gln Arg His Asn
            340                 345                 350

Glu Ala Leu Asn Gly Leu Arg Gln Ala Pro Ser Ser Tyr Pro Pro Thr
    355                 360                 365

Trp Pro Pro Gly Pro Ala His Ser Cys His Gln Ser Asn Ser Asn
    370                 375                 380
```

-continued

```
Gly His Arg Leu Cys Pro Thr His Val Tyr Ala Ala Pro Glu Gly Lys
385                 390                 395                 400
Ala Pro Ala Asn Ser Pro Arg Gln Gly Asn Ser Lys Asn Val Leu Leu
                405                 410                 415
Ala Cys Pro Met Asn Met Tyr Pro His Gly Arg Ser Gly Arg Thr Val
            420                 425                 430
Gln Glu Ile Trp Glu Asp Phe Ser Met Ser Phe Thr Pro Ala Val Arg
        435                 440                 445
Glu Val Val Glu Phe Ala Lys His Ile Pro Gly Phe Arg Asp Leu Ser
    450                 455                 460
Gln His Asp Gln Val Thr Leu Leu Lys Ala Gly Thr Phe Glu Val Leu
465                 470                 475                 480
Met Val Arg Phe Ala Ser Leu Phe Asn Val Lys Asp Gln Thr Val Met
                485                 490                 495
Phe Leu Ser Arg Thr Thr Tyr Ser Leu Gln Glu Leu Gly Ala Met Gly
            500                 505                 510
Met Gly Asp Leu Leu Ser Ala Met Phe Asp Phe Ser Glu Lys Leu Asn
        515                 520                 525
Ser Leu Ala Leu Thr Glu Glu Leu Gly Leu Phe Thr Ala Val Val
    530                 535                 540
Leu Val Ser Ala Asp Arg Ser Gly Met Glu Asn Ser Ala Ser Val Glu
545                 550                 555                 560
Gln Leu Gln Glu Thr Leu Leu Arg Ala Leu Arg Ala Leu Val Leu Lys
            565                 570                 575
Asn Arg Pro Leu Glu Thr Ser Arg Phe Thr Lys Leu Leu Leu Lys Leu
        580                 585                 590
Pro Asp Leu Arg Thr Leu Asn Asn Met His Ser Glu Lys Leu Leu Ser
    595                 600                 605
Phe Arg Val Asp Ala Gln
    610
```